(12) United States Patent
Cho et al.

(10) Patent No.: US 9,597,511 B2
(45) Date of Patent: Mar. 21, 2017

(54) METHOD TO ASSESS HEMODYNAMIC PERFORMANCE DURING CARDIAC RESYNCHRONIZATION THERAPY OPTIMIZATION USING ADMITTANCE WAVEFORMS AND DERIVATIVES

(71) Applicant: Medtronic, Inc., Minneapolis, MN (US)

(72) Inventors: Yong K. Cho, Maple Grove, MN (US); Douglas A. Hettrick, Andover, MN (US); Todd M. Zielinski, Ham Lake, MN (US)

(73) Assignee: Medtronic, Inc., Minneapolis, MN (US)

( * ) Notice: Subject to any disclaimer, the term of this patent is extended or adjusted under 35 U.S.C. 154(b) by 725 days.

(21) Appl. No.: 13/663,920

(22) Filed: Oct. 30, 2012

(65) Prior Publication Data

US 2013/0110188 A1    May 2, 2013

Related U.S. Application Data

(60) Provisional application No. 61/553,524, filed on Oct. 31, 2011.

(51) Int. Cl.
*A61N 1/365* (2006.01)
*A61N 1/368* (2006.01)

(52) U.S. Cl.
CPC ........ *A61N 1/36521* (2013.01); *A61N 1/3682* (2013.01); *A61N 1/3684* (2013.01); *A61N 1/3686* (2013.01)

(58) Field of Classification Search
CPC . A61N 1/36521; A61N 1/3684; A61N 1/3682
See application file for complete search history.

(56) References Cited

U.S. PATENT DOCUMENTS

5,305,745 A    4/1994 Zacouto
5,501,702 A    3/1996 Plicchi
(Continued)

FOREIGN PATENT DOCUMENTS

WO    9612440 A1    2/1996

OTHER PUBLICATIONS

Khoury DS, "Ambulatory monitoring of congestive heart failure by multiple bioelectric impedance vectors", JACC, Mar. 24, 2009; vol. 53(12).

(Continued)

*Primary Examiner* — Mark W Bockelman
(74) *Attorney, Agent, or Firm* — Carol F. Barry (57) ABSTRACT

An implantable medical device and associated method to determine an optimal control parameter setting for controlling a cardiac therapy that includes a therapy delivery module to deliver cardiac pacing signals at a plurality of pacing rates, and an admittance measurement module to determine admittance signals associated with each of the plurality of pacing rates. A control unit determines metrics of hemodynamic performance corresponding to each of the plurality of pacing rates in response to the determined admittance signals, identifies pacing rates of the plurality of pacing rates as rejected rates in response to the determined metrics of hemodynamic performance, and determines a pacing rate of the plurality of pacing rates as an optimal rate for delivering the cardiac therapy in response to the identified pacing rates.

32 Claims, 9 Drawing Sheets

(56) References Cited

U.S. PATENT DOCUMENTS

| | | | |
|---|---|---|---|
| 5,755,742 A | 5/1998 | Schuelke | |
| 5,843,137 A | 12/1998 | Condie | |
| 5,902,325 A | 5/1999 | Condie | |
| 6,044,297 A | 3/2000 | Sheldon | |
| 6,073,048 A | 6/2000 | Kieval | |
| 6,418,346 B1 | 7/2002 | Nelson | |
| 6,442,433 B1 | 8/2002 | Linberg | |
| 6,473,640 B1 | 10/2002 | Erlebacher | |
| 6,480,745 B2 | 11/2002 | Nelson | |
| 6,599,250 B2 | 7/2003 | Webb | |
| 7,096,064 B2 | 8/2006 | Deno | |
| 7,181,284 B2 | 2/2007 | Burnes | |
| 7,254,442 B2 | 8/2007 | van Gelder | |
| 7,657,313 B2 | 2/2010 | Rom | |
| 7,672,718 B2 | 3/2010 | Stahmann | |
| 7,706,879 B2 | 4/2010 | Burnes | |
| 7,769,451 B2 | 8/2010 | Yang | |
| 7,899,526 B2 | 3/2011 | Benditt | |
| 7,974,691 B2 | 7/2011 | Zhang | |
| 8,478,402 B2 | 7/2013 | Wahlstrand et al. | |
| 8,639,328 B2 | 1/2014 | Hettrick et al. | |
| 8,868,185 B2 | 10/2014 | Zielinski et al. | |
| 9,295,404 B2 | 3/2016 | Valvano et al. | |
| 2001/0012953 A1* | 8/2001 | Molin et al. | 607/9 |
| 2005/0080460 A1 | 4/2005 | Wang | |
| 2006/0271121 A1 | 11/2006 | Ding | |
| 2006/0287600 A1 | 12/2006 | Mceowen | |
| 2007/0270707 A1 | 11/2007 | Belalcazar | |
| 2008/0249583 A1 | 10/2008 | Salo et al. | |
| 2008/0262361 A1 | 10/2008 | Gutfinger | |
| 2009/0012416 A1 | 1/2009 | Belacazar | |
| 2009/0036777 A1 | 2/2009 | Zhang | |
| 2009/0048637 A1 | 2/2009 | Ni | |
| 2009/0062730 A1 | 3/2009 | Woo | |
| 2009/0069708 A1 | 3/2009 | Hattlestad | |
| 2009/0198302 A1 | 8/2009 | Anderson | |
| 2009/0275854 A1 | 11/2009 | Zielinski | |
| 2009/0276025 A1 | 11/2009 | Burnes | |
| 2010/0004714 A1 | 1/2010 | Georgakopoulos | |
| 2010/0113888 A1 | 5/2010 | Cho | |
| 2010/0113890 A1 | 5/2010 | Cho | |
| 2010/0114204 A1 | 5/2010 | Burnes et al. | |
| 2011/0022127 A1 | 1/2011 | Averina | |
| 2011/0190654 A1 | 8/2011 | Hettrick | |
| 2013/0110190 A1 | 5/2013 | Cho et al. | |

OTHER PUBLICATIONS (PCT/US2012/066810) PCT Notification of Transmittal of the International Search Report and the Written Opinion of the International Searching Authority, mailed Feb. 18, 2013, 9 pages.

* cited by examiner

METHOD TO ASSESS HEMODYNAMIC PERFORMANCE DURING CARDIAC RESYNCHRONIZATION THERAPY OPTIMIZATION USING ADMITTANCE WAVEFORMS AND DERIVATIVES

CROSS-REFERENCE TO PRIORITY APPLICATION

The present application claims priority and other benefits from U.S. Provisional Patent Application Ser. No. 61/553,524, filed Oct. 31, 2011, incorporated herein by reference in its entirety.

CROSS-REFERENCE TO RELATED APPLICATION

Cross-reference is hereby made to the commonly-assigned related U.S. application Ser. No. 13/663,951, entitled "METHOD TO ASSESS HEMODYNAMIC PERFORMANCE DURING CARDIAC RESYNCHRONIZATION THERAPY OPTIMIZATION USING ADMITTANCE WAVEFORMS AND DERIVATIVES", to Cho, et al., filed concurrently herewith and incorporated herein by reference in its entirety.

FIELD OF THE DISCLOSURE

The disclosure relates generally to medical devices and, in particular, to an apparatus and method for monitoring admittance signals for use in optimizing a cardiac therapy.

BACKGROUND

Cardiac resynchronization therapy (CRT) is a treatment for heart failure patients in which one or more heart chambers are electrically stimulated (paced) to restore or improve heart chamber synchrony. Improved heart chamber synchrony is expected to improve hemodynamic performance of the heart, such as measured by ventricular pressure and the rate of change in ventricular pressure or other measures. Achieving a positive clinical benefit from CRT is dependent on several therapy control parameters such as the atrioventricular (AV) delay and the ventricular-ventricular (VV) delay. The AV delay controls the timing of ventricular pacing pulses relative to an atrial depolarization, intrinsic or paced. The ventricular-ventricular (VV) delay controls the timing of a pacing pulse in one ventricle relative to a paced or intrinsic sensed event in the other ventricle.

Numerous methods for selecting optimal AV and VV delays for use in controlling CRT pacing pulses have been proposed. For example, clinicians may select an optimal AV or VV delay using Doppler echocardiography. Such clinical techniques are time-consuming and require an expert technician to perform. A need remains for automated methods which can be implemented in the CRT device for performing measurements correlated to the hemodynamic function of the heart and identifying optimal CRT control parameters.

DETAILED DESCRIPTION

In the following description, references are made to illustrative embodiments. It is understood that other embodiments may be utilized without departing from the scope of the disclosure. As used herein, the term "module" refers to an application specific integrated circuit (ASIC), an electronic circuit, a processor (shared, dedicated, or group) and memory that execute one or more software or firmware programs, a combinational logic circuit, or other suitable components that provide the described functionality.

Figure 1:
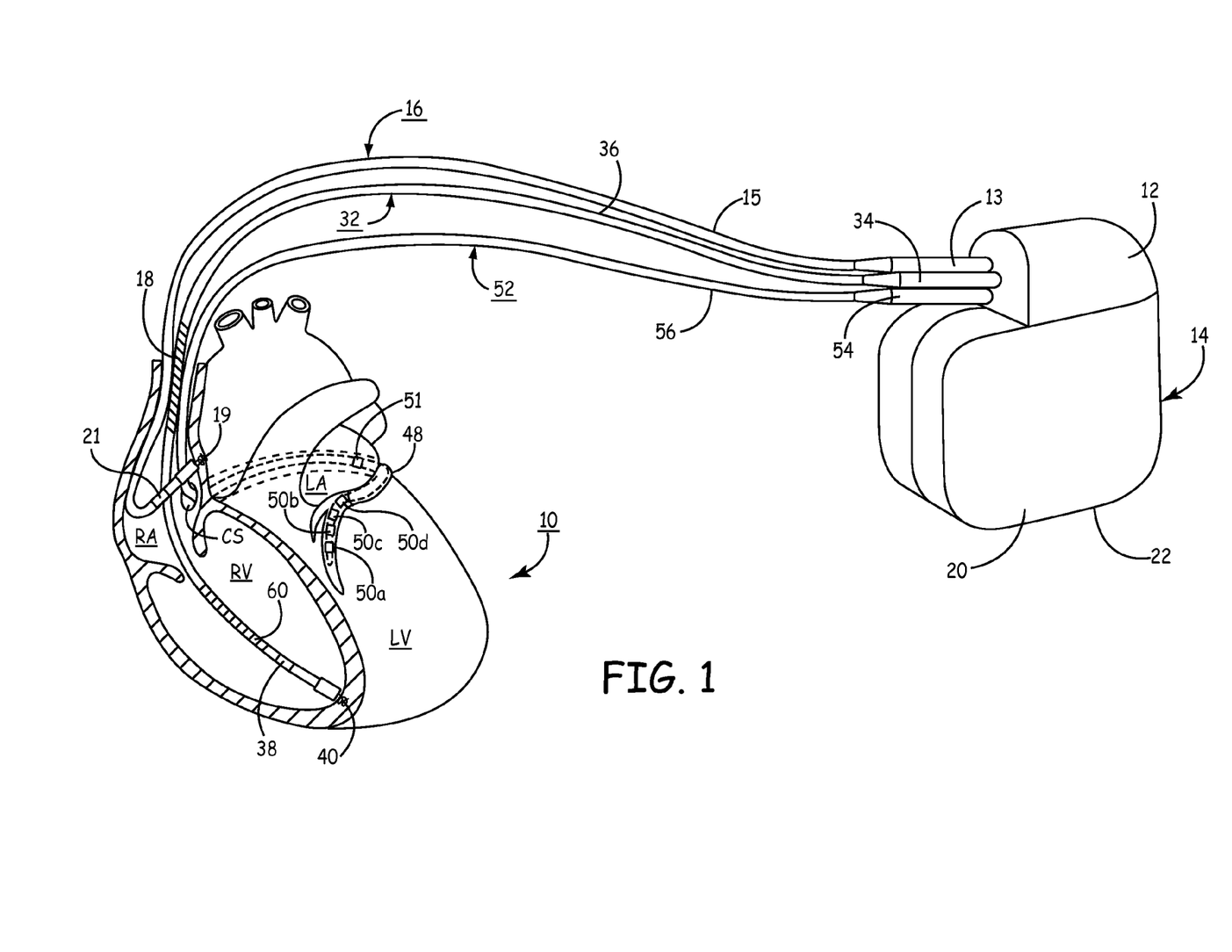
FIG. 1 depicts an implantable medical device (IMD) in which monitoring and pacing methods described herein may be implemented.

FIG. 1 depicts an implantable medical device (IMD) 14 in which monitoring and pacing methods described herein may be implemented. Various embodiments may be implemented in numerous types of implantable medical devices configured to sense admittance signals, such as pacemakers, implantable pacemaker cardioverter defibrillators (ICDs), ECG monitors, and hemodynamic monitors. One example of an implantable device capable of measuring cardiac impedance signals (admittance being the inverse of impedance) is described in commonly-assigned U.S. Pat. No. 5,843,137 (Condie et al.), hereby incorporated herein by reference in its entirety.

In the embodiment shown in FIG. 1, IMD 14 is provided for sensing intrinsic heart activity and delivering cardiac stimulation pulses in the form of pacing, cardioversion or defibrillation therapy, as appropriate, to one or more heart chambers. IMD 14 is configured to generate electrical signals for pacing the heart 10 or for delivering neurostimulation for treating heart failure or other cardiac therapies. In one embodiment, such therapies include CRT. In the illustrative embodiments described herein, admittance signals are used to optimize CRT control parameters. It is recognized however that other therapy control parameters may be optimized, using the techniques described herein, based on admittance signals.

IMD 14 is shown in communication with a patient's heart 10 by way of three leads 16, 32 and 52. The heart 10 is shown in a partially cut-away view illustrating the upper heart chambers, the right atrium (RA) and left atrium (LA), and the lower heart chambers, the right ventricle (RV) and left ventricle (LV), and the coronary sinus (CS) in the right atrium leading into the great cardiac vein 48, which branches to form inferior cardiac veins. Leads 16, 32 and 52 connect IMD 14 with the RA, the RV and the LV, respectively. Each lead has at least one electrical conductor and pace/sense electrode. A remote indifferent can electrode 20 is formed as part of the outer surface of the IMD housing 22. The pace/sense electrodes and the remote indifferent can electrode 20, also referred to herein as the "housing electrode" 20, can be selectively employed to provide a number of unipolar and bipolar pace/sense electrode combinations for pacing and sensing functions.

RA lead 16 is passed through a vein into the RA chamber. RA lead 16 is formed with a connector 13 fitting into a connector bore of IMD connector block 12 for electrically coupling RA tip electrode 19 and RA ring electrode 21 to IMD circuitry, enclosed within housing 22, via insulated conductors extending within lead body 15. RA tip electrode 19 and RA ring electrode 21 may be used in a bipolar fashion, or in a unipolar fashion with the IMD housing electrode 20, for achieving RA stimulation and sensing of RA EGM signals.

RV lead 32 is passed through the RA into the RV where its distal end carries RV tip electrode 40 and RV ring electrode 38 provided for electrical stimulation in the RV and sensing of RV EGM signals. RV lead 32 optionally carries high-voltage coil electrodes 18 and 60 for delivering high voltage cardioversion/defibrillation pulses to heart 10 in response to the detection of tachycardia or fibrillation. RV lead 32 is formed with a connector 34 fitting into a corresponding connector bore of IMD connector block 12. The coil electrodes 60 and 18 may be used in some embodiments for sensing cardiac signals, which may include cardiac EGM signals and admittance signals. Connector 34 is coupled to electrically insulated conductors within lead body 36 and connected with distal tip electrode 40, ring electrode 38 and coil electrodes 18 and 60.

Coronary sinus (CS) lead 52 is shown as a quadripolar lead passed through the RA, into the CS and further into a cardiac vein 48 to extend the electrodes 50a through 50d alongside the lateral free wall of the LV chamber to achieve LV stimulation and sensing of LV EGM signals. The LV CS lead 52 is coupled at the proximal end connector 54 into a bore of IMD connector block 12 to provide electrical coupling of conductors extending from electrodes 50a-50d within lead body 56 to IMD internal circuitry. In some embodiments, LV CS lead 52 could bear one or more proximal LA pace/sense electrode 51 positioned along CS lead body 56 such that it is disposed proximate the LA for use in stimulating the LA and/or sensing LA EGM signals.

Any of the electrodes carried by leads 16, 32 and 52 and housing 22 may be used for recording admittance signals. Admittance is the reciprocal of impedance, and thus any implantable medical device including impedance measurement circuitry and an adequate number of electrodes in operative relation to heart 10 may be adapted to perform the therapy control parameter optimization techniques described herein. Admittance increases with an increase in blood volume and decreases with a decrease in blood volume.

While a particular IMD system with associated leads and electrodes is illustrated in FIG. 1, numerous implantable cardiac monitoring, pacemaker and IMD system configurations are possible, which may include one or more leads deployed in intra-vascular, extra-vascular, intra-thoracic and extra-thoracic or subcutaneous locations. In some embodiments, leadless electrodes incorporated along the IMD housing may be used for sensing cardiac signals attendant to the depolarization of the myocardial tissue and admittance signals correlated to cardiac chamber blood volume. The lead and electrode arrangements will depend on the particular IMD system in which the presently disclosed techniques are implemented.

IMD 14 is shown as a multi-chamber device capable of sensing and stimulation in three or all four heart chambers. For descriptions of methods and devices that may be implemented for delivering CRT, reference is made to commonly-assigned U.S. Pat. No. 7,254,442 (van Gelder et al.), U.S. Pat. No. 7,181,284 (Burnes, et al.), and U.S. Pat. No. 7,706,879 (Burnes, et al.), all of which are hereby incorporated herein by reference in their entirety. It is understood that IMD 14 may be modified to operate as a single or dual chamber device. Furthermore, it is contemplated that the admittance monitoring techniques disclosed herein may be employed in a monitoring-only device that does not include therapy delivery capabilities. In some embodiments, IMD 14 may collect admittance signal data and transmit the data to an external programmer or another IMD for use in programming another device that is configured to deliver a therapy according to control parameters optimized using admittance signals.

Figure 2:
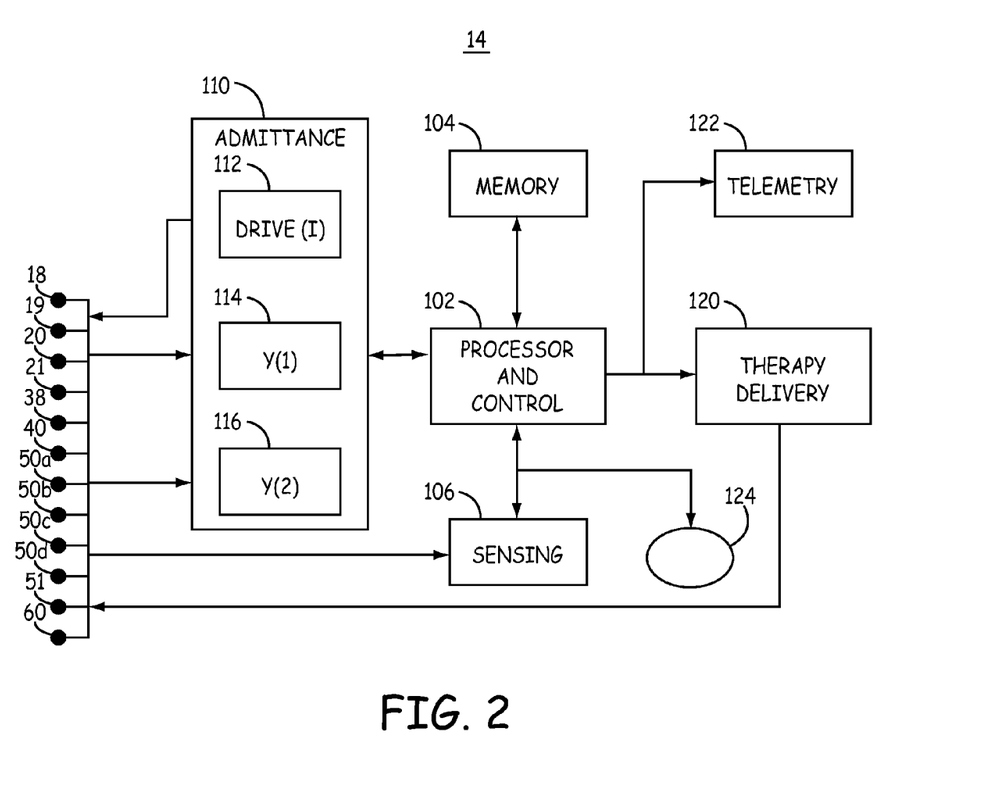
FIG. 2 is a functional block diagram illustrating one example configuration of the IMD shown in FIG. 1.

FIG. 2 is a functional block diagram illustrating one example configuration of IMD 14. IMD 14 includes a processor and control unit 102, memory 104, sensing module 106, therapy delivery module 120, and telemetry module 122. IMD 14 further includes admittance measurement module 110, which itself includes a drive signal generator 112 and measurement circuitry 114 and 116 for measuring a admittance signals Y(1) and Y(2). The measurement circuitry 114 and 116 records and inverts the voltage signal across a selected pair of monitoring electrodes in response to an applied drive current signal. Voltage signal changes are correlated to admittance changes. The voltage signal may be used directly as an "admittance signal" or converted to actual admittance using the known applied current signal. Measurement circuitry 114 and 116 may each include an inverter, amplifier, and filter for providing an admittance signal to processor and control 102.

Drive signal circuit 112 generates a non-excitatory current signal applied to an excitation pair of electrodes selected from electrodes 18, 19, 20, 21, 38, 40, 50a-50d, 51, and 60. A drive current signal may be applied to one or more excitation electrode pairs and the resulting voltage signal may be recorded across one or more recording electrode vectors simultaneously. Admittance signals may be sampled at a desired sampling rate over a predetermined interval of time to obtain a time-varying signal representing a changing blood volume in the recording electrode vector field.

In one embodiment, two admittance signals Y(1) and Y(2) are recorded using recording electrode vectors corresponding to a right ventricular blood volume and a left ventricular blood volume. In other embodiments, Y(1) and Y(2) may be recording using electrode vectors that correspond generally to two different ventricular vector fields. While recording two admittance signals Y(1) and Y(2) is indicated, one or more admittance signals may be recorded in various embodiments.

Admittance measurement module 110 may include a switch module for selecting which of electrodes 18, 19, 20, 21, 38, 40, 50a-50d, 51, and 60 are coupled to drive signal circuit 112 and which electrodes are coupled to measurement circuits 114 and 116. Measurement circuits 114 and 116 are each coupled to respective recording electrode pairs selected from electrodes 18, 19, 20, 21, 38, 40, 50a-50d, 51, and 60 for recording desired admittance signals. Bipolar measurement configurations may be used in which the non-excitatory drive current signal is applied across a pair of electrodes and a resulting voltage signal is measured across the same pair of electrodes. In other embodiments, a tripolar measurement configuration may be used in which a non-excitatory drive signal is applied across a first electrode pair and the resulting voltage signal is measured across a second electrode pair that shares a common electrode with the drive signal electrode pair. In still other embodiments, a quadripolar measurement configuration may be used in which two distinct electrode pairs are used for applying the drive current signal and recording the admittance signal. If CS lead 52 is provided as quadripolar lead for example, one pair of electrodes 50a through 50d may be used to provide the drive signal and another pair selected from electrodes 50a through 50d may be used to record a voltage signal in a quadripolar admittance measurement configuration.

Memory 104 may include computer-readable instructions that, when executed by processor and control 102, cause IMD 14 to perform various functions attributed throughout this disclosure to IMD 10 and processor 102. The computer-readable instructions may be encoded within memory 104. Memory 82 may comprise computer-readable storage media including any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital media.

Processor and control unit 102 may include any one or more of a microprocessor, a controller, a digital signal processor (DSP), an application specific integrated circuit (ASIC), a field-programmable gate array (FPGA), or equivalent discrete or integrated logic circuitry. In some examples, processor 102 may include multiple components, such as any combination of one or more microprocessors, one or more controllers, one or more DSPs, one or more ASICs, or one or more FPGAs, as well as other discrete or integrated logic circuitry. The functions attributed to processor 102 herein may be embodied as software, firmware, hardware or any combination thereof.

Processor and control unit 102 includes a therapy control unit that controls therapy delivery module 120 to deliver a therapy according to a selected one or more therapy programs, which may be stored in memory 104. Therapy delivery module 120 may include a signal generator electrically coupled to electrodes 18, 19, 20, 21, 38, 40, 50a-50d, 51, and 60, e.g., via conductors of the respective leads 16, 32 and 52, or, in the case of housing electrode 20, via an electrical conductor disposed within housing 22 of IMD 14. Therapy delivery module 120 may be configured to generate and deliver electrical stimulation therapy to heart 10 via selected combinations of electrodes 18, 19, 20, 21, 38, 40, 50a-50d, 51, and 60. In some embodiments, therapy delivery module 120 is configured to deliver cardiac pacing pulses for delivering cardiac resynchronization therapy (CRT), neurostimulation pulses, or other types of electrical stimulation therapy.

Therapy delivery module 120 may include a switch module (not shown) and processor and control 102 may use the switch module to select, e.g., via a data/address bus, which of the available electrodes 18, 19, 20, 21, 38, 40, 50a-50d, 51, and 60 are used to deliver electrical stimulation pulses and are coupled to signal generator included in therapy delivery module 120. The switch module may include a switch array, switch matrix, multiplexer, or any other type of switching device suitable to selectively couple a signal to selected electrodes.

In other embodiments, therapy delivery module 120 may include a fluid delivery pump for delivering a fluid to the patient, which may be a saline solution, pharmacological agent, or biological agent. When used to deliver a fluid, one of leads 16, 32, and 52 is modified to include a fluid delivery lumen or a separate fluid delivery catheter is coupled to therapy delivery module 120 to provide a fluid delivery path. Therapy delivery module 120 is optional and in some embodiments IMD 14 is provided as a monitoring device without therapy delivery capabilities and instead provides admittance data to another device for use in selecting optimal therapy delivery control parameters.

Sensing module 106 may be provided for receiving cardiac electrical signals from any of electrodes 18, 19, 20, 21, 38, 40, 50a-50d, 51, and 60 in order to monitor electrical activity of heart 10. Sensing module 106 may also include a switch module to select which of the available electrodes are used to sense the cardiac activity. In some examples, processor 102 selects the electrodes to function as sense electrodes, or the sensing vector, via the switch module within sensing module 106.

In an example embodiment, sensing module 106 includes multiple detection channels, each of which may be selectively coupled to respective combinations of electrodes 18, 19, 20, 21, 38, 40, 50a-50d, 51, and 60 to detect electrical activity of a particular chamber of heart 10. Each detection channel may comprise an amplifier that outputs an indication to processor 102 in response to sensing of a cardiac depolarization, in the respective chamber of heart 10. In this manner, sensing module 106 may detect the occurrence of R-waves and P-waves in the various chambers of heart 10 and processor and control 102 may use sensed event signals received from sensing module 106 for controlling therapy delivery 120. Sensing module 106 may further include digital signal processing circuitry for providing processor 102 with digitized EGM signals as needed for performing EGM signal analysis.

Sensing module 106 may additionally be coupled to other physiological sensors 124 for sensing signals useful in detecting a physiological condition of the patient. Sensors 124 may include, without limitation, an activity sensor, a posture sensor, a pressure sensor, an oxygen sensor, a temperature sensor or any combination thereof. Sensors 124 may be incorporated within or along the housing 22 of IMD 14 or be carried by a lead extending from IMD 14. In some embodiments, wireless sensors may be positioned remotely from IMD 14 and telemetry module 122 may receive transmitted data from a remote sensor and provide the sensor signal data to processor and control 102.

Sensors 124 may provide signals to sensing module 106 or directly to processor and control 102 for use in controlling admittance measurement module 110 or for use in interpreting admittance signals. For example, admittance signals may be acquired when the patient is known to be at rest or different levels of activity or heart rate.

Memory 104 stores algorithms, intervals, counters, or other data used by processor and control 102 to control IMD functions. In some embodiments, parameters stored in memory 104 are used to control the delivery of pacing pulses or other therapies delivered by therapy delivery module 120. Memory 104 is used to store admittance signals and/or data derived therefrom for use by processor and control 102 for selecting optimal therapy delivery parameters.

Telemetry module 122 provides communication with an external programmer or home monitor configured to communicate with IMD 14 via a wireless communication link. It is contemplated that IMD 14 may transmit to and receive programming data from an external programmer or home monitor that is coupled to a communications network for transferring data to a remote database or computer to allow remote management of a patient using the techniques described herein. Remote patient management systems may be configured to utilize the presently disclosed techniques to enable a clinician to review admittance signal data. Reference is made to commonly-assigned U.S. Pat. No. 6,599,250 (Webb et al.), U.S. Pat. No. 6,442,433 (Linberg et al.), U.S. Pat. No. 6,418,346 (Nelson et al.), and U.S. Pat. No. 6,480,745 (Nelson et al.) for general descriptions and examples of network communication systems for use with implantable medical devices for remote patient monitoring and device programming, all of which patents are incorporated herein by reference in their entirety.

A clinician may interact with a programmer (not shown) to transmit programming data to telemetry module 122 and to retrieve data from IMD 14 using an interrogation command. As such, an admittance measurement and therapy control parameter optimization protocol may be programmed into IMD 14 and acquired admittance-related data may be transmitted from IMD 14 to an external device using telemetry module 122.

Figure 3A:
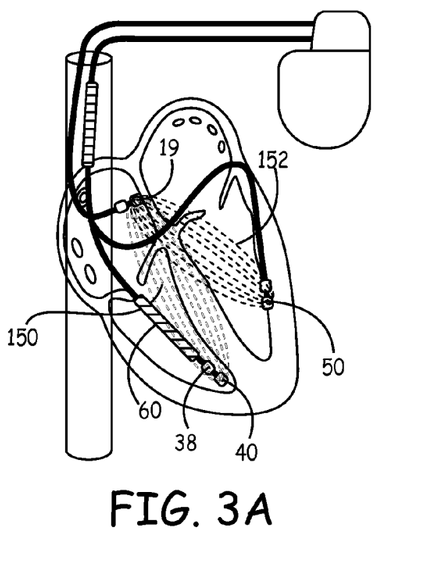
FIGS. 3A through 3D are schematic illustrations of possible electrode vector configurations that may be selected for recording admittance signals for use in optimizing a therapy control parameter.
Figure 3B:
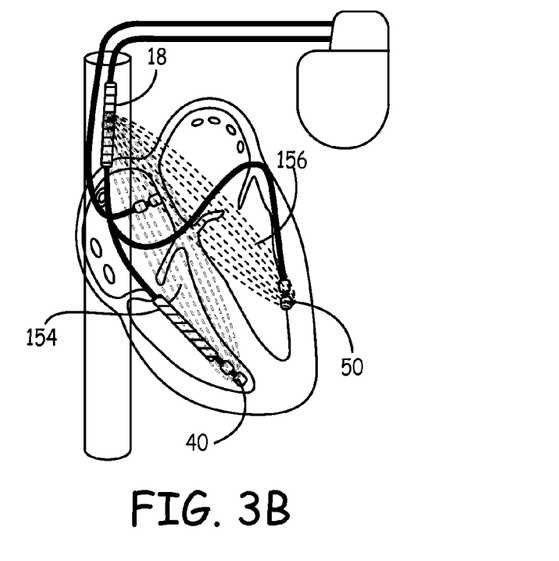

FIGS. 3A through 3D are schematic illustrations of possible electrode vector configurations that may be selected for recording admittance signals for use in optimizing a therapy control parameter. In FIGS. 3A and 3B, bipolar measurement configurations are shown in which a common electrode pair is used for both injecting the drive current signal and for measuring the resulting voltage signal which can be converted to an admittance signal by admittance measurement circuitry 114 and 116. In other embodiments, a different electrode pair may be used for injecting a drive current signal.

In FIG. 3A, recording electrode vector 150 is selected using the RV tip electrode 40 and RA tip electrode 19 for recording an admittance signal that is substantially correlated to RV blood volume. A second recording electrode vector 152 is selected between a CS lead electrode 50 (which may correspond to any of electrodes 50a through 50d when the CS lead is provided as a quadripolar lead) positioned along the LV lateral free wall and the RA tip electrode 19. This vector field 152 substantially correlates to the LV blood volume.

In the example of FIG. 3B, an RV admittance signal is recorded using the RV tip electrode 40 and SVC coil electrode 18 establishing recording vector field 154. An LV admittance signal is recorded using a CS lead electrode 50 and the SVC coil electrode 18.

Figure 3C:
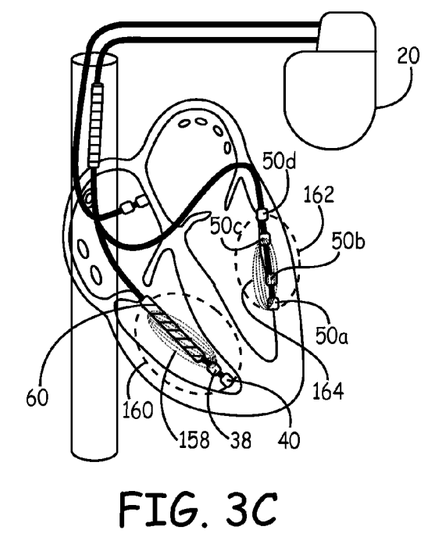

In FIG. 3C, an RV admittance signal is recorded by delivering a drive current signal between the RV tip electrode 40 and RV coil electrode 60 as represented by vector field 160 and recording the resulting voltage across the RV ring electrode 38 (see FIG. 3A) and RV coil electrode 60 as shown schematically by vector field 158. An LV admittance signal is recorded by delivering a drive current signal between a pair of LV electrodes, e.g. electrodes 50A and 50D along vector field 162, and the resulting voltage signal is recorded across another pair of LV electrodes, e.g. 50b and 50d, as shown by vector field 164.

Figure 3D:
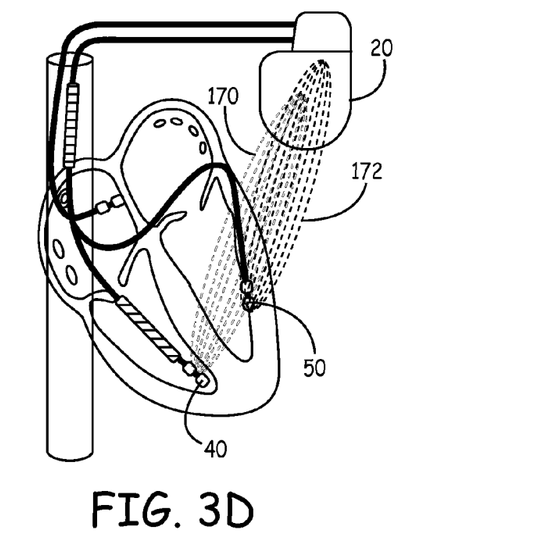

In FIG. 3D, an first admittance signal is recorded using the RV tip electrode 40 and housing electrode 20, along vector field 170, and a second admittance signal is acquired using a CS lead electrode 50 and housing electrode 20, along vector field 172. While a limited number of examples are shown here, it is recognized that numerous drive signal and recording electrode vectors may be selected from available electrodes. The vector fields are generally selected to achieve a high correlation between the admittance signal and one or both of the respective right or left ventricular volumes individually or combined. A recording electrode vector may extend between the RV and LV ventricles using combinations of electrodes on RV lead 36 and CS lead 52.

Figure 4:
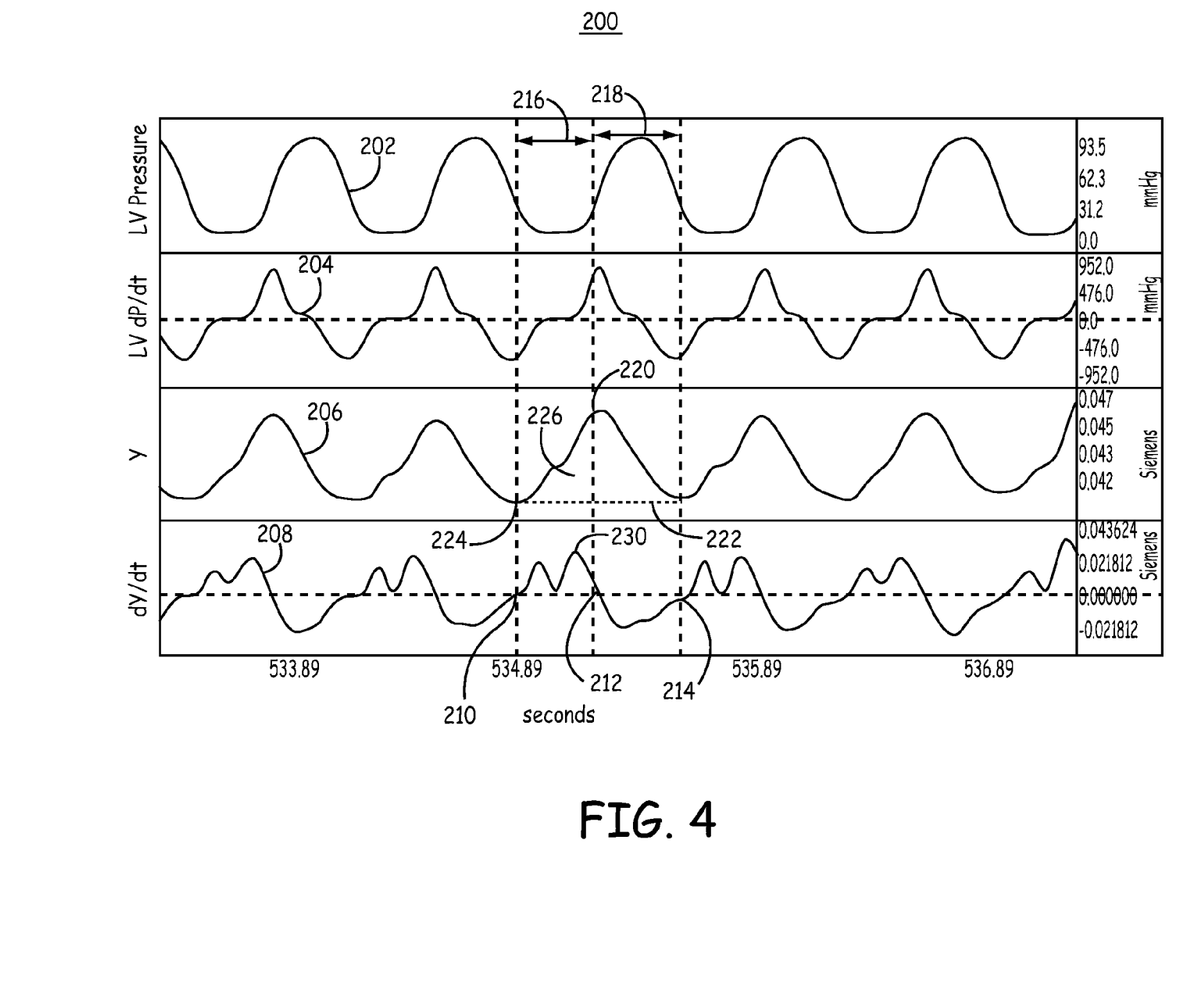
FIG. 4 is a plot of a left ventricular pressure signal and its first derivative and a ventricular admittance signal and the first derivative of the admittance signal.

FIG. 4 is a plot 200 of an LV pressure signal 202, LV dP/dt signal 204, a ventricular admittance signal Y 206, and the first derivative of the admittance signal dY/dt 208. In an example embodiment, the admittance signal 206 and dY/dt are recorded over multiple cardiac cycles then averaged over a cardiac cycle to determine surrogate metrics of hemodynamic performance of the heart. In other embodiments, fiducial points, such as maximums or minimums, are determined from the admittance signal 206 and/or dY/dt signal 208 during defined measurement windows and averaged over multiple cardiac cycles to obtain metrics of hemodynamic performance.

For example, since the admittance signal is proportional to chamber volume, then the time derivative of the admittance signal should be proportional to flow into and out of the chamber. Therefore, a positive going zero crossing 210 of the dY/dt signal 208 or the minimum peak 224 of the admittance signal 206 may define the start of the diastolic filling phase 216 of the cardiac cycle. The next negative-going zero crossing 212 of the dY/dt signal 208 or the next maximum peak 220 of the admittance signal 206 defines the end of diastole and the start of the systolic ejection phase 218, which ends at the next minimum Y or next positive-going dY/dt zero-crossing 214. The diastolic interval 216 defined by these fiducial points of the admittance signal 206 or dY/dt 208 is seen to correlate well to the diastolic filling phase as observed on the LV pressure signal 202. Likewise, the systolic interval 218 defined using zero-crossing points of dY/dt 208 or maximum and minimums of the admittance signal 206 correlates well to the systolic phase of the LV pressure signal 202. Thus the intervals 216 and 218 may be used to set measurement windows during which or at the endpoints of various measurements of the admittance signal 206 or dY/dt 208 may be determined.

Various hemodynamic metrics that may be determined from the admittance signal 206 include, but are not limited to, a maximum admittance 220, an area 226 bounded by the admittance signal 206 and a lower boundary 222 defined by the minimum admittance 224, the net change in admittance over a cardiac cycle (peak to peak amplitude), and a mean admittance. Additionally or alternatively, hemodynamic metrics may be determined using a peak dY/dt 230 or other features of the dY/dt signal. Other measurements that may be made from a cardiac impedance signal for use in optimizing a cardiac therapy control parameter are generally disclosed in commonly-assigned U.S. patent application Ser. No. 12/916,012, filed Oct. 29, 2010, hereby incorporated herein by reference in its entirety.

Figure 5:
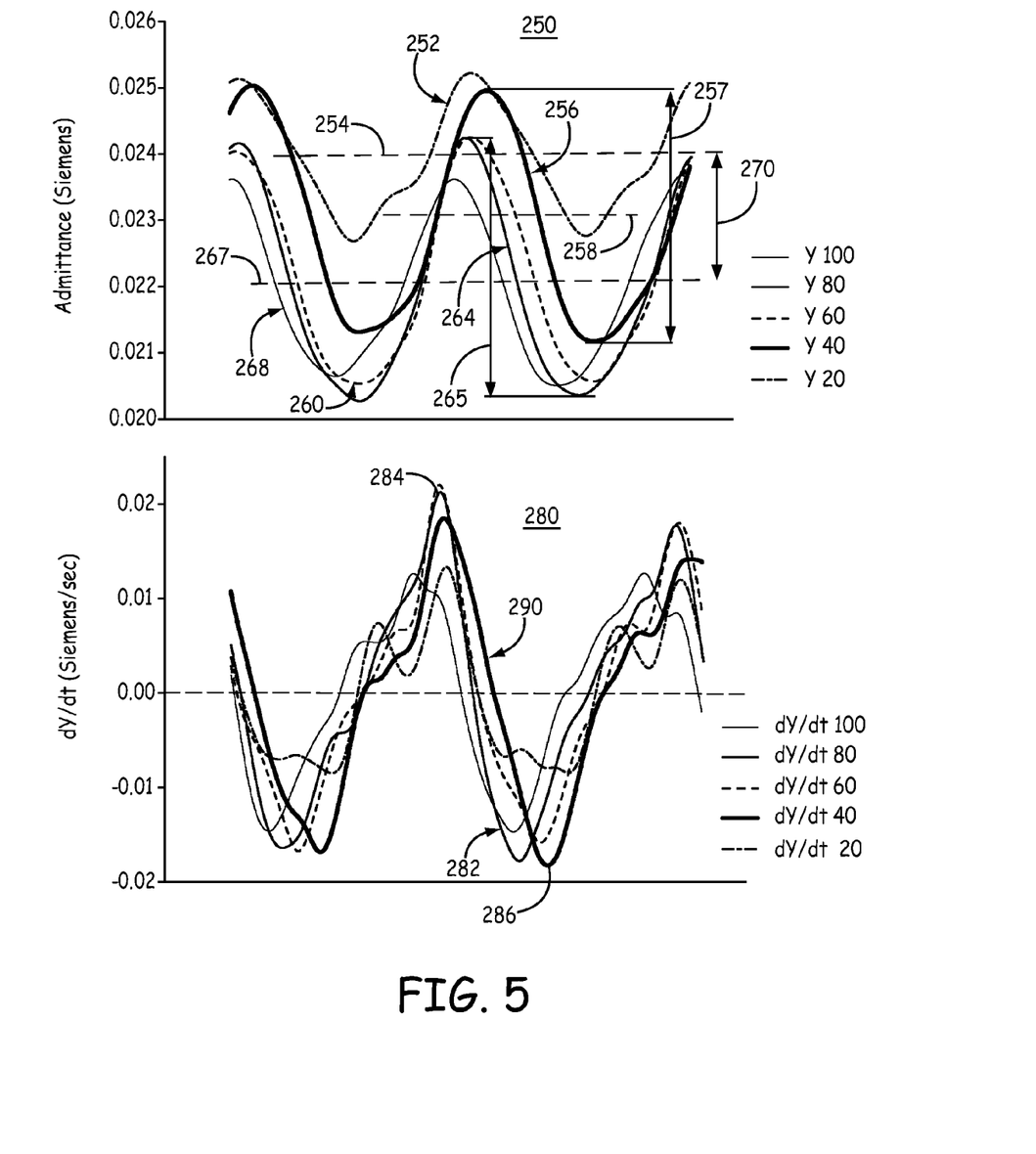
FIG. 5 is a graph of averaged admittance signals and a graph of the first derivative of the average admittance signals.

FIG. 5 is a graph 250 of averaged admittance signals and a graph 280 of the first derivative, dY/dt, of the average admittance signals shown in graph 250. The admittance signals 252, 256, 260, 264, and 268 plotted in graph 250 were obtained during pacing at multiple AV delays of 20, 40, 60, 80 and 100 ms, respectively. For example, the admittance signal 252, having a mean admittance 254 was obtained by averaging a ventricular admittance signal recorded over several cardiac cycles during pacing at an AV delay of 20 ms. The admittance signal 268 having a mean admittance 267 was obtained by averaging a ventricular admittance signal recorded during pacing at an AV delay of 100 ms. The admittance signals 252, 256, 260, 264, and 268 may be obtained using any of the electrode configurations discussed above. In this example, the admittance signals are recorded from the RV ring electrode to RV coil electrode during injection of a drive current signal between the RV tip electrode and the RV coil electrode.

A shift 270 in the mean admittance 254 during pacing at 20 ms AV delay is observed relative to the mean admittance 267 during pacing at 100 ms AV delay. A relative increase in mean admittance would correspond to greater ventricular volume, suggesting less efficient emptying of the ventricles during pacing at 20 ms AV delay as compared to pacing at 100 ms AV delay. As will be further described below, therapy control parameter settings that result in a relative increase in mean admittance, indicating increased end-diastolic and end-systolic volumes, may be rejected when selecting optimal therapy control parameters. This increase in mean admittance is a relatively short-term response to a change in programmed pacing therapy control parameters. It is measured over several cardiac cycles and compared to mean admittances measured over several cardiac cycles during different pacing parameter test settings. This increase in mean admittance as an acute response to a pacing control parameter change is distinct from a long-term increase in cardiac or thoracic admittance that would be associated with chronic worsening of congestive heart failure (heart dilation and/or pulmonary edema) which would occur gradually over a period of days, weeks, months or longer.

In graph 280, an average dY/dt signal obtained over several cardiac cycles for each of the AV pacing delays ranging from 20 ms to 100 ms is shown. In one example, after rejecting AV delay settings that result in a relative increase in mean admittance, the remaining AV delay settings are analyzed to identify a control parameter setting that results in the greatest maximum dY/dt 284 or maximum peak-to-peak difference between the maximum 284 and minimum 286. In this example, the maximum peak-to-peak difference is found for dY/dt signal 282 corresponding to an 80 ms AV delay, which may be selected as the optimal AV delay according to these criteria.

Referring again to graph 250, the average admittance signal 256 recorded during pacing at an AV delay of 40 ms has a similar peak-to-peak difference 257 as the peak-to-peak difference 265 of admittance signal 264 (80 ms AV delay) and the peak-to-peak difference (not shown by reference numeral in FIG. 5 for the sake of clarity) of admittance signal 260 (60 ms delay). The dY/dt signal 290 for a 40 ms AV delay results in a relatively large peak-to-peak difference as well, comparable to the peak-to-peak differences of dY/dt for 60 and 80 ms AV delays. Pacing at a 40 ms AV delay, however, produced a relatively high mean admittance 258 compared to the means of other admittance signals 260, 264 and 268 for example. As such, a mean admittance may be used as a first criterion in selecting optimal therapy control parameters. A mean admittance greater than a predefined threshold, an average of other mean admittance measurements, or some other baseline mean admittance measurement may be used to reject control parameter settings as causing increased end systolic and end diastolic volumes. Once settings that result in a relatively higher mean admittance are eliminated, other control parameter settings may be evaluated according to positive selection criteria.

Figure 6:
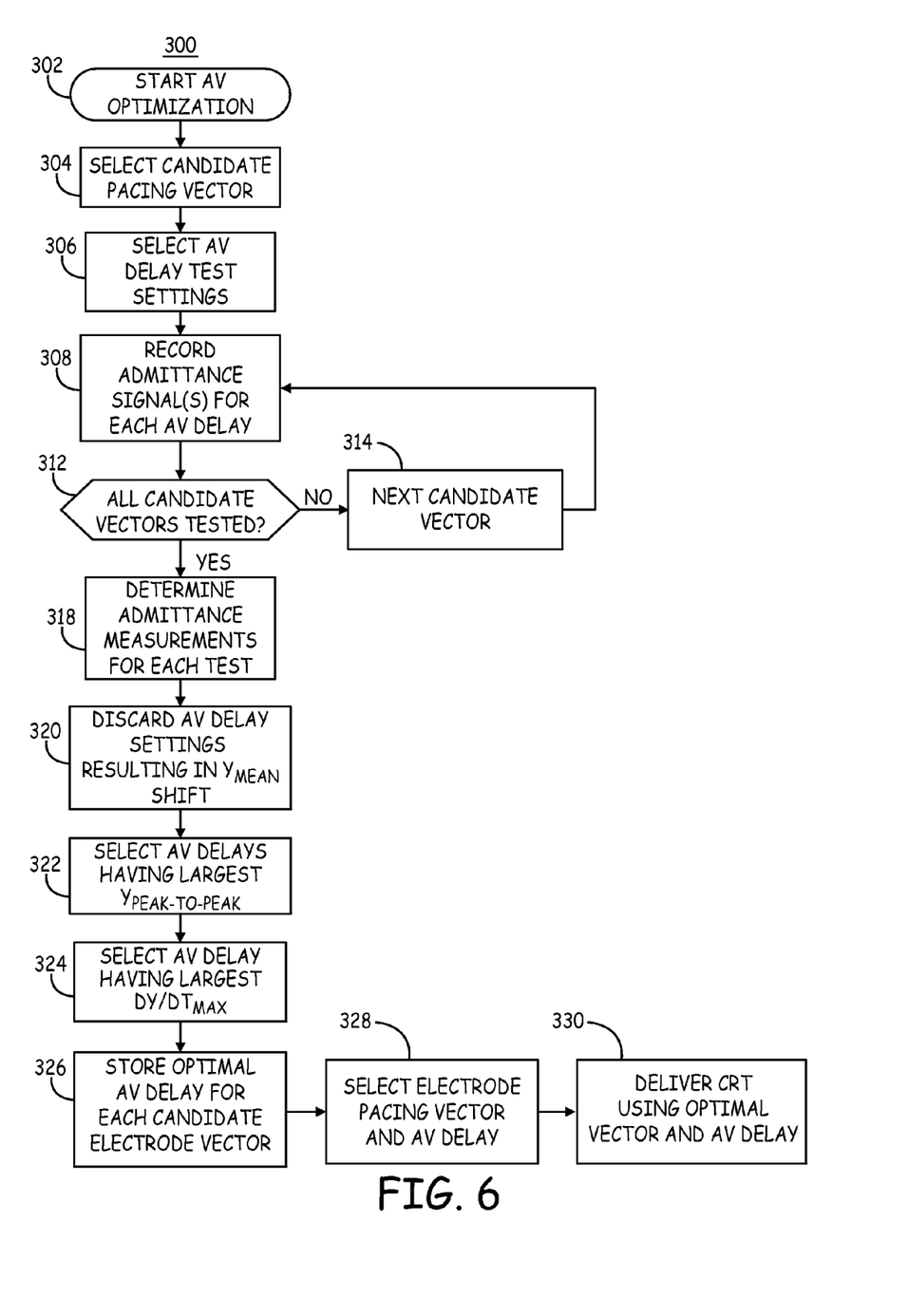
FIG. 6 is a flow chart of a method for selecting an optimal therapy control parameter using admittance signals according to one embodiment.

FIG. 6 is a flow chart 300 of a method for selecting an optimal therapy control parameter using admittance signals according to one embodiment. At block 302, an AV delay optimization process is initiated. In this example, AV delay used to control CRT is being optimized. In other embodiments, however, other control parameters for CRT or control parameters for other cardiac therapies may be optimized using the techniques described herein.

Flow chart 300 and other flow charts presented herein are intended to illustrate the functional operation of the medical device system, and should not be construed as reflective of a specific form of software or hardware necessary to practice the methods described. It is believed that the particular form of software, firmware and/or hardware will be determined primarily by the particular system architecture employed in the medical device and by the particular sensing and therapy delivery methodologies employed by the device. Providing software, firmware and/or hardware to accomplish the described functionality in the context of any modern IMD, given the disclosure herein, is within the abilities of one of skill in the art.

Methods described in conjunction with flow charts presented herein may be implemented in a computer-readable medium that includes instructions for causing a programmable processor to carry out the methods described. A "computer-readable medium" includes but is not limited to any volatile or non-volatile media, such as a RAM, ROM, CD-ROM, NVRAM, EEPROM, flash memory, and the like. The instructions may be implemented as one or more software modules, which may be executed by themselves or in combination with other software.

Control parameter optimization may be initiated at block 302 in response to a user command interacting with a programmer in telemetric communication with an IMD, automatically by the IMD on a periodic basis, or triggered in response to measurements indicating that therapy optimization may be needed, for example a worsening trend in other hemodynamic or cardiac function parameters monitored by the IMD. In some embodiments, a lead monitoring algorithm, capture threshold test, loss of capture monitoring or other self-diagnostic tests may result in a need to select a new pacing vector and new pacing control parameters for use in conjunction with a new pacing vector.

At block 304, a candidate pacing vector for delivering CRT is selected. In some embodiments, the CS lead 52 may be provided as a quadripolar or other multipolar lead enabling multiple LV pacing sites and vectors to be selected. During CRT delivery, biventricular pacing or LV-only pacing may be delivered. As such, if multiple LV pacing electrodes 50a through 50d are available, the LV pacing vector may be optimized by comparing admittance-based measurements for multiple candidate pacing vectors. In one example, multiple LV bipolar pacing vectors and/or LV unipolar pacing vectors utilizing electrodes 50a through 50d may be tested.

At block 306, the control parameter settings to be tested are selected. In the illustrative embodiment, AV delay settings ranging from zero to a maximum AV delay setting may be selected as the test settings. In one example, AV delay settings of 0 ms to 120 ms in 20 ms increments are selected though fewer or more AV delay settings could be tested over wider or narrower ranges and using different AV delay increments.

At block 308, the admittance signal is recorded for each AV delay setting during pacing using the selected candidate pacing vector. One or more admittance signals may be recorded using different recording electrode vectors. For example, an RV admittance signal and an LV admittance signal may be recorded. In other examples, multiple admittance signals corresponding to the RV, the LV, a combination of both RV and LV admittance, or any combination RV, LV and biventricular admittance signals may be recorded.

After recording the desired admittance signals for each AV delay setting, the next candidate pacing vector is selected randomly or in a preferred order at block 314. The admittance signals are recorded in IMD memory for each of the AV delay settings using the new candidate pacing vector at block 308. This process repeats until admittance signals have been recorded for all control parameter test settings for each candidate pacing vector, as determined at block 312.

At block 318, admittance-based measurements are determined from the recorded signals. Admittance measurements may include any of the measurements described in the foregoing, including any of, but not limited to, maximum peak admittance, mean admittance, minimum peak admittance, peak-to-peak admittance, maximum dY/dt, minimum dY/dt, peak-to-peak dY/dt, and mean dY/dt. As described previously, admittance-based measurements may be obtained using measurement time windows defined by dY/dt zero-crossings.

Any control parameter settings that result in a mean admittance ($Y_{mean}$) shift relative to an established baseline mean admittance are discarded at block 320. A baseline mean admittance may be a mean admittance of the combined admittance signals recorded for all test conditions. If a mean admittance measurement is a threshold amount greater than the baseline mean admittance, the corresponding test control parameter(s) are rejected.

From the remaining data, for each pacing vector, the AV delays resulting in the largest peak-to-peak differences in the admittance signal are identified. For example, the three AV delay settings resulting in the three largest peak-to-peak differences for each pacing vector may be identified. From these AV delay settings, the AV delay having the largest maximum peak dY/dt is selected at block 324 as the optimal AV delay for the given pacing vector. At block 326, the optimal AV delay for each candidate pacing vector is stored in IMD memory.

At block 328, a pacing vector for therapy delivery is selected. The pacing vector may be selected manually and programmed by a user. In some embodiments, the pacing vector may be selected automatically based on capture threshold, lead impedance, or other pacing vector selection criteria. In still other embodiments, the pacing vector for therapy delivery may be selected using the admittance-based measurements. The pacing vector resulting in the greatest peak-to-peak difference of the admittance signal and/or largest dY/dt maximum peak for the identified optimal AV delay and not resulting in a positive threshold shift in mean impedance may be selected as the therapy delivery pacing vector at block 328. The optimal AV delay for the corresponding selected pacing vector may be retrieved from memory and automatically programmed when the pacing vector is selected and programmed (either automatically or manually) as the pacing vector for therapy delivery. At block 330, CRT is delivered using the selected pacing vector and corresponding optimal AV delay.

In some embodiments, selection of an optimal AV delay and optimal pacing vector or other optimal therapy delivery control parameter may include identifying the optimal parameter setting(s) and transmitting recommended settings to an external programmer or other device for review by a clinician. The clinician may review the recommended settings and admittance data retrieved from the IMD and program the desired therapy delivery control parameters using this information.

Figure 7:
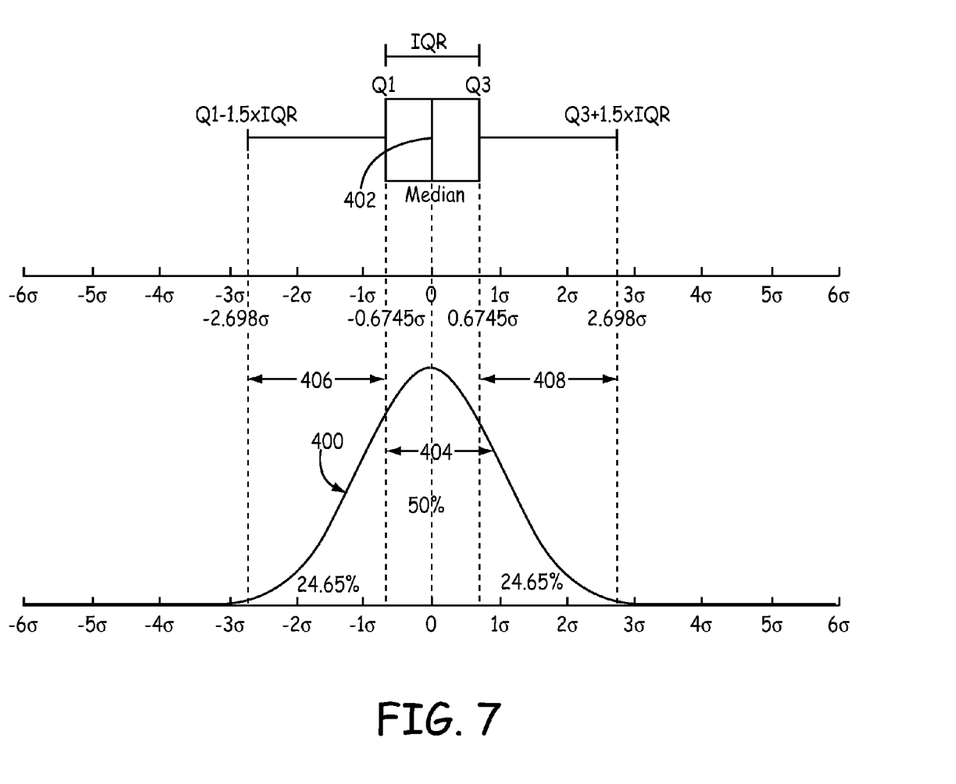
FIG. 7 is a frequency plot of the mean admittance for a range of AV delay test settings.

FIG. 7 is a frequency plot 400 of the mean admittance for a range of AV delay test settings. The mean admittances measured over a cardiac cycle for all AV delay test settings are plotted in a frequency plot 400 to determine the median 402 of the mean admittance measurements. Ranges of the mean admittance plot may be defined based on median value 402 for rejecting AV delay settings. In one example, any AV delay settings resulting in mean admittance measurements more than one standard deviation greater than the median 402 are rejected. These AV delay settings produce a positive shift in the mean admittance suggesting higher end diastolic and end systolic volumes and less efficient ejection of blood from the ventricular chambers.

Ranges of mean admittance used to reject AV delay settings may include a range greater than the median 402 and/or less than the median 402. In one example, an interquartile range 404 is defined which includes 50% of the mean admittance measurements included in frequency plot 400. In plot 400, the interquartile range 404 encompassing 50% of the mean admittance measurements is defined as the median±0.6745σ (where σ is one standard deviation of the median). A recommended or automatically programmed AV delay setting will be selected from the AV delay settings corresponding to the mean admittance measurements occurring in the interquartile range 404. AV delay settings resulting in mean admittance measurements in the lower quartile range 406 and in the upper quartile range 408 will be rejected as being non-optimal AV delay settings based on the mean admittance difference relative to the median mean admittance 402.

It is contemplated that numerous criteria may be defined for rejecting AV delay settings (or other control parameter settings) based on a computed median value of the mean admittance measurements or more generally based on frequency plot 400. In some embodiments, at least a portion of the upper quartile range 408 of mean admittances is used to reject corresponding AV delay settings. A portion of one or both of the upper quartile range 408 and the lower quartile range 406 of the mean admittance measurements may be used for rejecting therapy control parameter settings.

Additional criteria may be applied to the non-rejected AV delay settings for positively selecting a recommended or automatically programmed setting. In one embodiment, the AV delay resulting in the greatest peak-to-peak difference in admittance and a mean admittance measurement falling in the interquartile range 404 is selected as the optimal AV delay. In another embodiment, the AV delay resulting in the greatest maximum peak dY/dt and a mean admittance falling in the interquartile range 404 is selected as the optimal AV delay.

Figure 8:
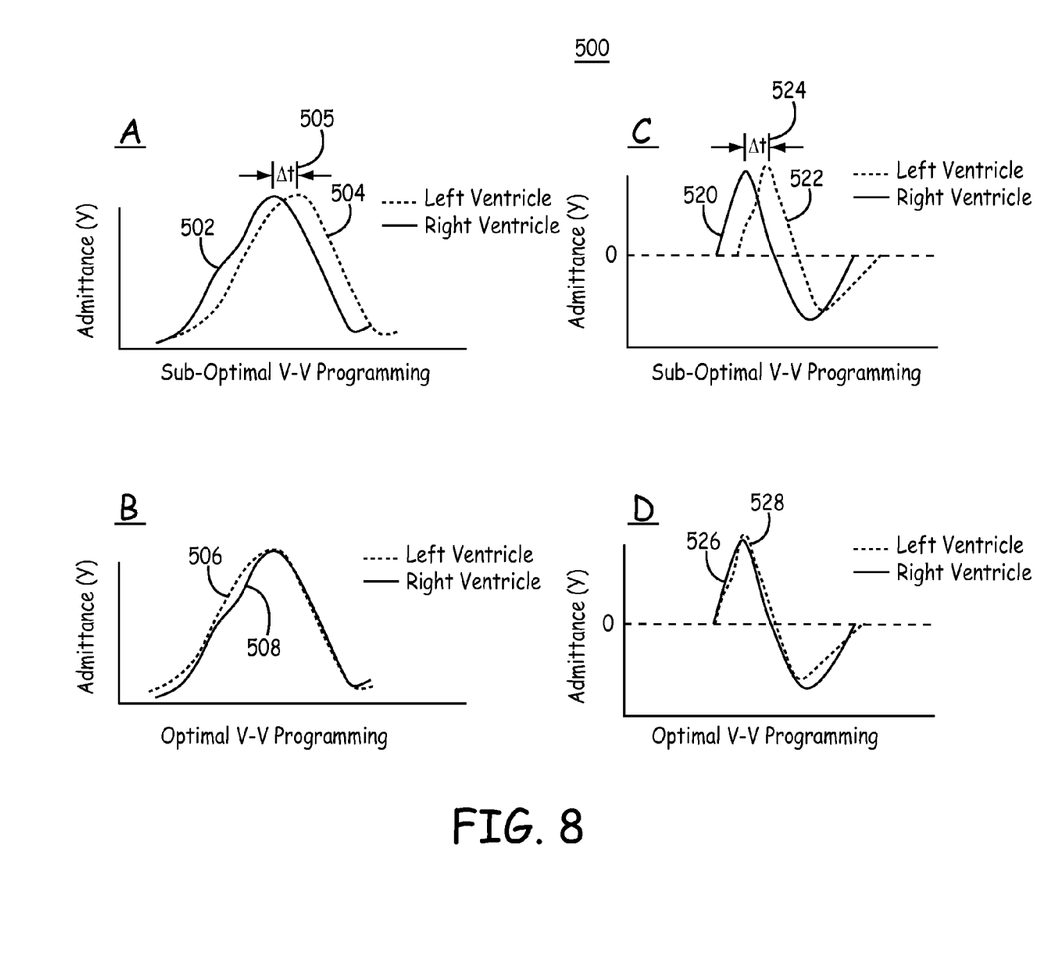
FIG. 8 is a depiction of left and right ventricular admittance and first derivative plots corresponding to sub-optimal and optimal inter-ventricular (VV) delay settings.

FIG. 8 is a depiction of left and right ventricular admittance and first derivative dY/dt plots 500 corresponding to sub-optimal and optimal interventricular (VV) delay settings. Right ventricular admittance signals 502 and 508 represent admittance signals acquired during two different VV delay settings. In panel A, the LV admittance signal 504 lags the RV admittance signal 502 by a time interval 505, based on the timing of the maximum peak amplitudes of the two signals. The time interval 505 between the maximum peak amplitudes is measured as a phase delay between the RV and LV admittance signals. When VV delay is optimized, as shown in panel B, the LV and RV admittance signals 506 and 508, respectively, are substantially synchronous, i.e. in phase, with a negligible or non-significant delay between the two maximum signal peaks.

Similarly, in panel C, the LV dY/dt signal 522 lags the RV dY/dt signal 520 by a time interval 524, i.e. the phase difference, based on the relative time occurrences of the maximum positive dY/dt signal peaks. When VV delay is optimized, as shown in panel D, maximum peak dY/dt is substantially synchronized, i.e. no phase delay, between the RV and LV dY/dt signals 526 and 528, respectively. As such, time intervals between fiducial points identified along the admittance or dY/dt signals, as shown in this example, may be used to select optimal control parameters.

Figure 9:
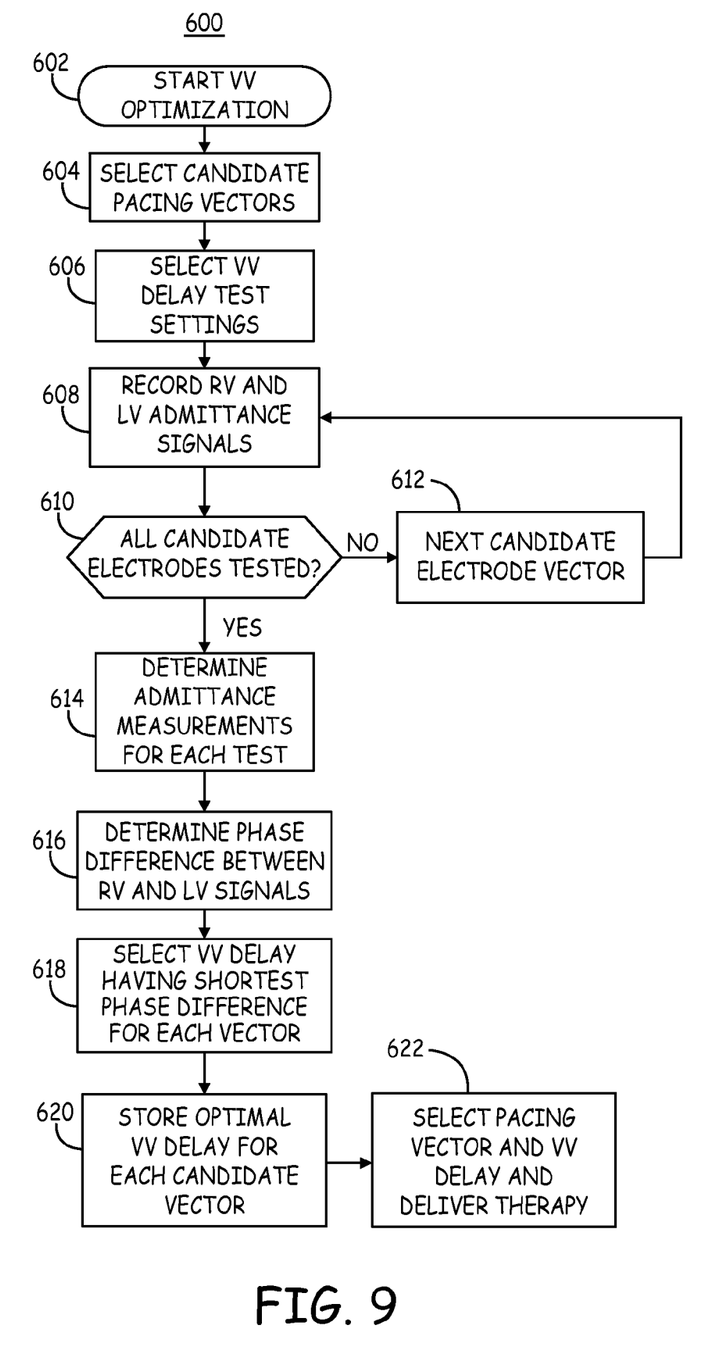
FIG. 9 is a flow chart of one method for selecting an optimal VV delay setting according to an illustrative embodiment.

FIG. 9 is a flow chart 600 of one method for selecting an optimal VV delay setting according to an illustrative embodiment. The VV delay optimization procedure is initiated at block 602, either manually or automatically in response to another monitored signal as described previously. At block 604, a candidate pacing vector is selected. As described previously, if a multipolar lead is implemented, multiple candidate pacing vectors may be available for testing.

At block 606, a range and number of VV delay settings are selected to be tested. RV and LV admittance signals are sensed and recorded for each test VV delay setting while delivering biventricular or single ventricle pacing pulses using the candidate pacing vector selected at block 604. The RV admittance signal may be recorded using the example measurement vectors described in conjunction with FIGS. 3A-3D or any available vector that provides an admittance signal correlated to the right ventricular volume and pressure. The LV admittance signal may be recorded using the example measurement vectors described in conjunction with FIGS. 3A-3D or any available vector that provides an admittance signal correlated to the left ventricular volume and pressure. These signals may be recorded simultaneously using a common or shared electrode in the drive signal and/or measurement electrode vector or distinct electrode vectors.

After recording the RV and LV admittance signals for each VV delay setting, the next candidate electrode vector for delivering ventricular pacing pulses is selected at block 612 until all candidate vectors have been tested at block 610. Candidate vectors could include different LV pacing vectors used with a defined, fixed RV pacing vector or different LV pacing vectors used in different combinations with different RV pacing vectors or different LV pacing vectors during no RV pacing, i.e. LV-only pacing.

At block 614, measurements are determined from the admittance signals for use in optimal VV delay and pacing vector selection. Such measurements may include any amplitude-related or time-related (phase) measurements determined from the admittance signals or first derivatives. At block 616, a time difference between fiducial points of the RV and LV admittance signals or first derivatives thereof is determined. As described in conjunction with FIG. 8, the time difference between the peak admittances in the RV and LV or the time difference between the peak dY/dt in the RV and LV may be measured. These measurements are determined using the stored admittance signals acquired for each test VV delay setting for each candidate pacing vector configuration.

At block 618, a VV delay resulting in the shortest time measured at block 616 is selected as the optimal VV delay for a given candidate pacing vector configuration. The optimal VV delay for each candidate vector configuration is stored at block 620. At block 622, a pacing vector configuration is selected for therapy delivery. The selected pacing vector configuration is one that results in the shortest measured time difference between the fiducial points derived from the RV and LV admittance or dY/dt signals, indicating mechanical synchrony between the ventricles. The optimal VV delay stored for the selected pacing vector is either automatically programmed and therapy is delivered or the recommended pacing configuration and VV delay are provided to a clinician, for example via a programmer or other external device in communication with the IMD.

Thus, an IMD system and associated method for determining optimal therapy control parameters based on admittance signals have been presented in the foregoing description with reference to specific embodiments. It is appreciated that various modifications to the referenced embodiments may be made without departing from the scope of the disclosure as set forth in the following claims.

The invention claimed is:

1. A medical device for delivering a cardiac therapy, comprising:
   a therapy delivery module to deliver cardiac pacing signals at a plurality of pacing rates;
   an admittance measurement module to determine admittance signals associated with each of the plurality of pacing rates; and
   a control unit configured to:
   determine a first metric of hemodynamic performance corresponding to each of the plurality of pacing rates in response to the determined admittance signals,
   identify pacing rates among the plurality of pacing rates as rejected rates in response to the first metrics of hemodynamic performance determined for each of the respective pacing rates,
   determine a second metric of hemodynamic performance from the admittance signals for respective ones of the plurality of pacing rates not identified as rejected rates, the second metric of hemodynamic performance different than the first metric, and
   responsive to the determined second metrics, determine an optimal pacing rate for delivering the cardiac therapy from among the plurality of pacing rates not identified as rejected rates.

2. The medical device of claim 1, wherein each of the plurality of pacing rates is one of a plurality of predetermined atrioventricular delays.

3. The medical device of claim 1, the control unit further configured to determine the first metric as a mean admittance for each of the plurality of pacing rates over a plurality of cardiac cycles during delivery of the cardiac pacing signals, determine relative shifts between the determined mean admittances, and identify pacing rates of the plurality of pacing rates as rejected rates in response to the determined relative shifts between the mean admittances.

4. The medical device of claim 3, wherein the control unit is further configured to determine the second metric by determining a maximum peak to minimum peak difference of the admittance signal for each of the pacing rates of the plurality of pacing rates other than the rejected rates, compare the determined maximum peak to minimum peak differences determined for the respective plurality of pacing rates not identified as rejected rates, and determine the optimal pacing rate of the plurality of pacing rates in response to a maximum one of the maximum peak to minimum peak differences.

5. The medical device of claim 4, the control unit further configured to determine a measurement window for determining the maximum peak to minimum peak difference of the admittance signals, wherein determining the measurement window comprises:
   determining a minimum peak of the admittance signal as a first endpoint;
   determining a maximum peak of the admittance signal as a second endpoint; and
   determining the measurement window in response to the first endpoint and the second endpoint.

6. The medical device of claim 3, the control unit further configured to determine a median of the determined mean admittances, determine a range of the determined mean admittances relative to the determined median, and identify pacing rates of the plurality of pacing rates as rejected rates in response to the determined range.

7. The medical device of claim 6, wherein the range comprises a portion of an upper quartile range.

8. The medical device of claim 6, wherein the range comprises a portion of an lower quartile range.

9. The medical device of claim 1, further comprising a plurality of electrodes coupled to the therapy delivery module and the admittance measurement module, wherein the cardiac pacing signals are delivered via the plurality of electrodes, the admittance measurement module further configured to deliver a signal between a first pair of electrodes of the plurality of electrodes positioned along a left ventricle of a patient's heart, and determine the admittance signals between a second pair of electrodes of the plurality of electrodes positioned along the left ventricle of the patient's heart.

10. The medical device of claim 1, further comprising a plurality of electrodes coupled to the therapy delivery module and the admittance measurement module, wherein the cardiac pacing signals are delivered via the plurality of electrodes, the admittance measurement module configured to determine the admittance signals by determining a first admittance signal between a first pair of electrodes of the plurality of electrodes positioned to be correlated to right ventricular blood volume for each of the plurality of pacing rates, and by determining a second admittance signal sensed between a second pair of electrodes of the plurality of electrodes positioned to be correlated to left ventricular blood volume for each of the plurality of pacing rates.

11. The device of claim 1 wherein the admittance measurement module comprises impedance measurement circuitry.

12. The device of claim 1 wherein the admittance measurement module comprises means for applying a first electrical signal to heart tissue and means for measuring a second electrical signal from the heart tissue during application of the first electrical signal.

13. The device of claim 12 wherein the first electrical signal comprises a known current and wherein the second electrical signal comprises a measured voltage.

14. A method of delivering a cardiac therapy, comprising:
  delivering cardiac pacing signals at a plurality of pacing rates;
  determining admittance signals associated with each of the plurality of pacing rates;
  determining a first metric of hemodynamic performance corresponding to each of the plurality of pacing rates in response to the determined admittance signals determined for each of the respective pacing rates;
  identifying pacing rates among the plurality of pacing rates as rejected rates in response to the determined first metrics of hemodynamic performance;
  determining a second metric of hemodynamic performance from the admittance signals for respective ones of the plurality of pacing rates not identified as rejected rates, the second metric of hemodynamic performance different than the first metric, and
  responsive to the determined second metrics, determining an optimal pacing rate for delivering the cardiac therapy, the optimal pacing rate determined from among the plurality of pacing rates not identified as rejected rates.

15. The method of claim 14, wherein each of the plurality of pacing rates is one of a plurality of predetermined atrioventricular delays.

16. The method of claim 14, further comprising:
  determining the first metric as a mean admittance for each of the plurality of pacing rates over a plurality of cardiac cycles during delivery of the cardiac pacing signals;
  determining relative shifts between the determined mean admittances; and
  identifying pacing rates of the plurality of pacing rates as rejected rates in response to the determined relative shifts between the mean admittances.

17. The method of claim 16, further comprising:
  determining the second metric by determining a maximum peak to minimum peak difference of the admittance signals for each of the pacing rates of the plurality of pacing rates other than the rejected rates;
  comparing the determined maximum peak to minimum peak differences determined for the respective plurality of pacing rates not identified as rejected rates; and
  determining the optimal pacing rate of the plurality of pacing rates in response to a maximum one of the maximum peak to minimum peak differences.

18. The method of claim 17, further comprising determining a measurement window for determining the maximum peak to minimum peak difference of the admittance signals, wherein determining the measurement window comprises:
  determining a minimum peak of the admittance signal as a first endpoint;
  determining a maximum peak of the admittance signal as a second endpoint; and
  determining the measurement window in response to the first endpoint and the second endpoint.

19. The method of claim 16, further comprising:
  determining a median of the determined mean admittances;
  determining a range of the determined mean admittances relative to the determined median; and
  identifying pacing rates of the plurality of pacing rates as rejected rates in response to the determined range.

20. The method of claim 19, wherein the range comprises a portion of an upper quartile range.

21. The method of claim 19, wherein the range comprises a portion of an lower quartile range.

22. The method of claim 14, wherein the cardiac pacing signals are delivered via a plurality of electrodes, the method further comprising:
  delivering a signal between a first pair of electrodes of the plurality of electrodes positioned along a left ventricle of a patient's heart; and
  determining the admittance signals between a second pair of electrodes of the plurality of electrodes positioned along the left ventricle of the patient's heart.

23. The method of claim 14, wherein the cardiac pacing signals are delivered via a plurality of electrodes, the method further comprising:
  delivering a first admittance signal between a first pair of electrodes of the plurality of electrodes positioned to be correlated to right ventricular blood volume; and
  determining a second admittance signal sensed between a second pair of electrodes of the plurality of electrodes positioned to be correlated to left ventricular blood volume.

24. The method of claim 14 wherein determining the admittance signals comprises impedance employing impedance measurement circuitry.

25. The method of claim 14 wherein determining the admittance signals comprises applying a first electrical signal to heart tissue and measuring a second electrical signal from the heart tissue during application of the first electrical signal.

26. The method of claim 25 wherein the first electrical signal comprises a known current and wherein the second electrical signal comprises a measured voltage.

27. A medical device for delivering a cardiac therapy, comprising:
- a therapy delivery module configured to deliver cardiac pacing signals at a plurality of pacing delay intervals;
- an admittance measurement module configured to acquire admittance signals for each of the plurality of pacing delay intervals; and
- a control unit configured to:
    - determine a first admittance metric for each of the plurality of pacing delay intervals from the acquired admittance signals,
    - compare the first admittance for each of the plurality of pacing delay intervals to rejection criteria;
    - identify an interval of the plurality of pacing delay intervals as a rejected delay interval if the first admittance metric determined for the respective delay interval meets the rejection criteria;
    - determine a second admittance metric for each of the plurality of pacing delay intervals not identified as a rejected delay interval;
    - compare the second admittance metrics; and
    - identify an optimal pacing delay interval for delivering the cardiac therapy from the plurality of pacing delay intervals not identified as rejected delay intervals in response to the comparison of the second admittance metrics.

28. The device of claim 27, wherein the control module is configured to:
- determine the first admittance metric by determining a mean admittance for each of the plurality of pacing delay intervals;
- identify a rejected delay interval of the plurality of pacing delay intervals if the mean admittance exceeds a mean admittance threshold;
- for each of the plurality of pacing delay intervals not identified as a rejected delay interval, determine the second admittance metric of the admittance signal acquired for the respective pacing delay interval;
- identify a largest one of the second admittance metrics; and
- identify the optimal pacing delay interval by identifying one of the plurality of pacing delay intervals not identified as a rejected interval and having the largest one of the second admittance metrics.

29. The device of claim 27, wherein the control module is further configured to:
- determine the first admittance metric by determining a mean admittance for each of the plurality of pacing delay intervals;
- identify a rejected delay interval of the plurality of pacing delay intervals if the mean admittance exceeds a mean admittance threshold;
- identify a first portion of the plurality of pacing delay intervals having second admittance metrics greater than second admittance metrics of a second portion of the plurality of pacing delay intervals;
- for each of the plurality of pacing delay intervals of the first portion not identified as a rejected delay interval, determine a third admittance metric of the admittance signal acquired for the respective pacing delay interval; and
- identify the optimal pacing delay interval by identifying one of the first portion of the plurality of pacing delay intervals having a greatest value of the third admittance metric.

30. The device of claim 27 wherein the admittance measurement module comprises impedance measurement circuitry.

31. The device of claim 27 wherein the admittance measurement module comprises means for applying a first electrical signal to heart tissue and means for measuring a second electrical signal from the heart tissue during application of the first electrical signal.

32. The device of claim 31 wherein the first electrical signal comprises a known current and wherein the second electrical signal comprises a measured voltage.

* * * * *